United States Patent [19]

Boissevain et al.

[11] Patent Number: 4,786,817
[45] Date of Patent: Nov. 22, 1988

[54] SYSTEM AND METHOD FOR MEASUREMENT OF TRAVELING WEBS

[75] Inventors: Mathew G. Boissevain, Los Altos Hills; Leonard M. Anderson, San Jose; Michael K. Norton, Saratoga, all of Calif.

[73] Assignee: Measurex Corporation, Cupertino, Calif.

[21] Appl. No.: 33,749

[22] Filed: Apr. 3, 1987

Related U.S. Application Data

[63] Continuation-in-part of Ser. No. 902,225, Aug. 29, 1986.

[51] Int. Cl.⁴ .......................................... G01N 21/31
[52] U.S. Cl. .................................. 250/571; 250/339; 356/429
[58] Field of Search ............... 250/571, 572, 559, 562, 250/563, 339, 341, 359.1, 360.1; 356/429, 430, 431, 434, 435; 162/198, 263, DIG. 6

[56] References Cited

U.S. PATENT DOCUMENTS

| | | | |
|---|---|---|---|
| 3,655,980 | 4/1972 | Bossen | 162/198 |
| 3,806,730 | 4/1974 | Tirkkonen et al. | 250/359.1 |
| 3,965,356 | 6/1976 | Howarth | 250/339 |
| 4,006,358 | 2/1977 | Howarth | 162/198 |
| 4,300,049 | 10/1981 | Sturm | 250/339 |
| 4,577,104 | 3/1986 | Sturm | 250/341 |

Primary Examiner—Edward P. Westin
Attorney, Agent, or Firm—Burns, Doane, Swecker & Mathis

[57] ABSTRACT

A system and method for optically measuring parameters including dry basis weight, basis weight and moisture content of fibrous sheet materials during manufacture without scanning. The system includes means for reflecting modulated light as parallel rays perpendicularly incident upon one surface of a traveling web, and means to detect light transmitted through the web at least four distinct bands of wavelengths.

14 Claims, 4 Drawing Sheets

SYSTEM AND METHOD FOR MEASUREMENT OF TRAVELING WEBS

RELATED APPLICATION

This application is a continuation-in-part of our prior application Ser. No. 902,225, filed Aug. 29, 1986, bearing the same title.

BACKGROUND OF THE INVENTION

1. Field of the Invention

The present invention generally relates to a system and method for measuring properties of traveling webs of fibrous sheet material during manufacture and, more particularly, to a system and method for providing measurements such as dry basis weight, basis weight, and moisture content of fibrous sheet materials.

2. State of the Art

In the manufacture of sheet materials, important parameters for process and quality control include basis weight and moisture content. Basis weight is normally defined as the weight per unit area of sheet material and is usually stated in units of grams per square meter. Dry basis weight, a related measure that is particulary useful during the manufacture of fibrous sheet materials such as paper and cardboard, refers to weight per unit area of sheet material excluding moisture. In the art of paper-making, dry basis weight is equivalent to the weight of dry material, primarily fibers, comprising a given area of a paper sheet. Moisture content refers to the amount of moisture per unit area of a sheet. These parameters are related by the fact that, for a given area of a sheet, basis weight minus moisture content equals dry basis weight.

It is well known that dry basis weight can be determined by laboratory tests but that such tests have several inherent drawbacks. One shortcoming of laboratory tests is that substantial time is required for sample acquisition and analysis; during that time, substantial quantities of sheet material may be produced and production conditions may change sufficiently that the laboratory test results, when available, may no longer be representative of the conditions of the manufacturing process or product. Another drawback of laboratory tests is that samples obtained for testing may not completely represent sheet material that has been produced; this is because samples are often obtained only at the end of a sheet roll and, therefore, may not be representative of paper quality at intermediate locations along the roll.

To detect the composition of sheet materials, it is known to direct a beam of light or other radiation of known wavelength against a surface of a given area of sheet material and to measure the radiation absorbed by the sheet. Generally speaking, the amount of absorbed radiation at a particular wave length is a function of the composition of the sheet material; for example, the cellulose content of paper sheet material is indicated by the absorption of infrared light having a wavelength of about 1.5 microns.

Various devices have been proposed for making parametric measurements of properties of traveling webs of sheet material on-line. The term "on-line" in this art refers to measurements that are made on a sheet-making machine while the machine is operating. The phrase "parametric measurements" as used herein refers to measurements of physical properties whose values determine characteristics and qualities of the sheet material. Thus, parametric measurements of paper and similar fibrous sheet materials may include basis weight, dry basis weight, moisture content, thickness, and transmissivity.

In paper-making processes, on-line parametric measurements are difficult to make accurately. The difficulties arise, in part, because modern paper-making machines are large and operate at high speeds. For example, some conventional paper-making machines produce sheets which are 100 to 400 inches wide at the rate of about 20 to 100 feet per second. Furthermore, on-line measurements in paper-making processes are often problematical because of severe environmental conditions; for example, the environment around a paper-making machine may include a high concentration of wet pulp and a humid atmosphere that contains water droplets and air-borne particles of sulfuric acid or alkalies. Regardless of such conditions, however, practical on-line measuring devices on sheet-making machines must operate continuously for extended periods and their repair and maintenance must be accomplished without causing substantial down-time to the sheet-making machines.

To provide on-line parametric measurements of paper and other fibrous sheet materials, workers in the art have proposed various sensors that periodically traverse or "scan" traveling webs of sheet material in the cross-direction. (In the sheet-making art, the direction of sheet travel is known as the "machine direction" and the direction across a sheet that is perpendicular to the machine direction is known as the "cross direction"). For example, U.S. Pat. Nos. 3,641,349; 3,681,595; 3,757,122; and 3,886,036 assigned to Measurex Corporation discuss basis weight gauges of the scanning type. Also, U.S. Pat. No. 4,289,964, assigned to Intec Corporation, suggests that beta ray gauges can scan slowly across a traveling web in the cross direction to determine basis weight. Further, the patent to Intec suggests that beta ray gauges can be augmented with laser, infrared, or ultraviolet light sensors to indicate transmissive qualities across the web.

Despite numerous advantages of scanning gauges in sheet-making operations, such gauges have limitations. For example, the moving parts in scanning gages can cause repair and maintenance problems. Also, scanning gauges that require relatively long periods to make successive measurements are not optimal for control purposes that require a relatively large number of measurements over relatively short periods. For instance, conventional scanning gages for detecting the basis weight and moisture content of fibrous sheet materials normally require about thirty seconds to obtain a series of measurements over a traveling sheet in the cross direction. (A series of such measurements in the cross-direction are said to provide a "profile" of the sheet.)

In view of the limitations of scanning devices, it has been proposed to mount a plurality of fixed sensors to detect parameters at locations distributed along the cross-direction of a traveling web of fibrous sheet material. In particular, U.S. Pat. No. 3,806,730 suggests a measuring device that includes a set of tubes mounted to distribute light onto the surface of a moving web in the cross direction. According to the patent, the tubes are rectangular aluminum pipes that have bright interior surfaces to carry light. A set of similar tubes is positioned to receive and detect light transmitted through the web. The device described in the patent is said to be useful for measuring parameters such as basis weight and moisture content of paper sheet materials.

As further background to the present invention, it is useful to generally describe a typical paper-making process. Generally speaking, a paper-making process begins when a slurry of fibers and water, called raw stock, is spread onto a supporting wire mesh from a reservoir called a head box. The wire mesh supports the fibers while allowing substantial drainage. To uniformly spread raw stock onto a wire mesh, it is customary to employ gate-like devices mounted next to one another in the cross direction at the so-called slice lip openings of the head box. Then after raw stock has been discharged through the slice lip openings to form a wet web on a wire mesh, the web is passed through a press section that squeezes water from the web. Then, the web is passed through a dryer section to evaporate water from the web. After the dryer section, the web passes through calendar rollers and, usually, through a scanner and onto a reel. The portion of the paper-making process prior to the dryer section is often referred to as the wet end of the process. It can be appreciated that measurements at the wet end are highly desirable because such measurements may provide early control in the paper production process and, thus, may minimize wastage by indicating needed process changes before substantial quantities of substandard paper are produced. On the other hand, wet end measurements are difficult to make because of the high water content, of paper webs at this stage and severe environmental conditions.

OBJECTS AND SUMMARY OF THE PRESENT INVENTION

Generally speaking, an object and advantage of the present invention is to provide an improved method and system to detect properties of traveling webs of sheet material for use with a supervisory control system for a paper-making machine to allow rapid actuation of control slice openings and other production controls.

More particularly, an object of the present invention is to provide an improved system and rapid method for providing parametric measurements of properties, such as dry basis weight and moisture content, across profiles of traveling webs of sheet material without scanning the webs.

In accordance with the preceding objects, the preferred embodiment of the present invention generally provides a system including the following components: illuminating means to transmit substantially parallel rays of light generally perpendicularly onto one surface of a traveling web simultaneously and uniformly across substantially the entire width of the web; a plurality of light detection devices to receive parallel rays of light that are transmitted through the web at least at four distinct narrow bands of wavelengths; an enclosure to provide environmental isolation of the illuminating means and the detection devices; and signal processing means to indicate the quantity of light received by the detection devices at identifiable locations. In a particular embodiment, the enclosure includes first and second ducts that have transparent walls mounted to extend transversely across opposite faces of the traveling web. In one of the ducts, the illuminating means transmits collimated beams of light to reflectors that reflect the beams as parallel rays generally perpendicularly incident upon the surface of the web. In the other duct, the light detection devices receive parallel rays transmitted through the web at four distinct narrow bands of wavelengths.

Further, the present invention provides an improved method for optically determining properties of traveling webs of sheet material rapidly and without scanning. The method includes the steps of providing modulated beams of collimated light; reflecting parallel rays from the collimated beams generally perpendicularly onto the surface of a traveling web across substantially the entire width of the web at least at four distinct narrow bands of wavelengths; detecting rays transmitted through the traveling web; and providing electrical output signals proportional to the intensity of detected light at identifiable locations.

The foregoing and other aspects of the present invention can be readily ascertained by reference to the following description and attached drawings which illustrate the preferred embodiment.

DETAILED DESCRIPTION OF THE PREFERRED EMBODIMENT

Figure 1:
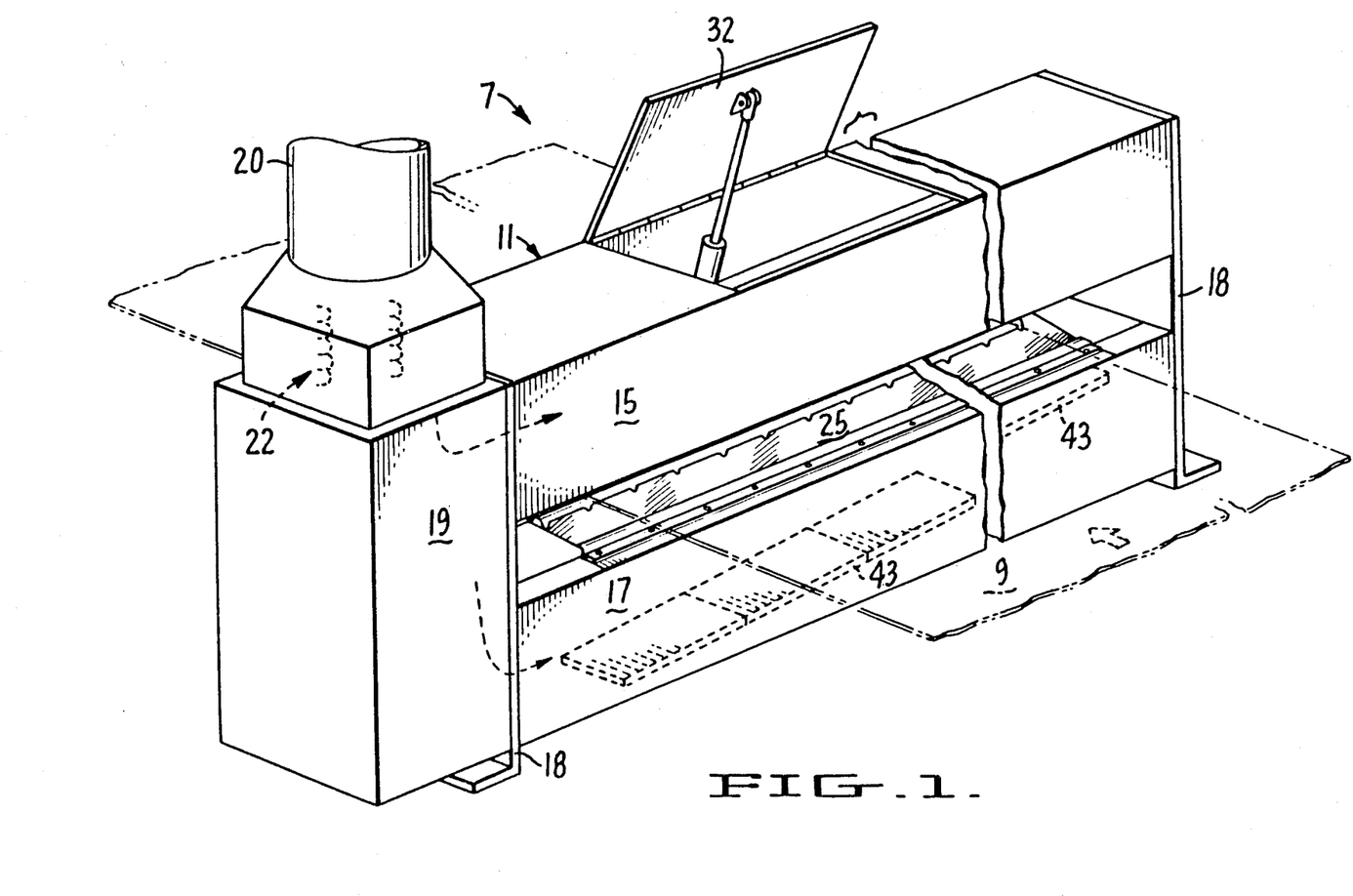
FIG. 1 is a pictorial view of the exterior of a housing of a machine that operates according to the present invention. In this drawing some internal components of the machine are generally indicated by dashed lines.

FIG. 1 shows a machine, generally indicated by the numeral 7, for providing parametric measurements of a web 9 of sheet material traveling horizontally through the machine in the direction indicated by the arrow. A particular feature of machine 7 is that measurements of parameters of web 9 such as basis weight, dry basis weight and moisture content can be made for a full profile of web 9 without scanning the web. Machine 7 generally includes a housing that protectively isolates measurement instruments and components in ducts 15 and 17. In the illustrated embodiment, ducts 15 and 17 are supported at their opposite ends by upstanding stanchions 18. In typical installations, ducts 15 and 17 range in length from about 100 inches to about 400 inches and are spaced apart vertically by a distance of about eight inches to allow clearance for web 9 to travel between the ducts. Although machine 7 can be installed on a paper-making machine at any convenient location between a first press section and a windup roll, the housing of the machine is particularly adapted for installation near the first press section.

Figure 2:
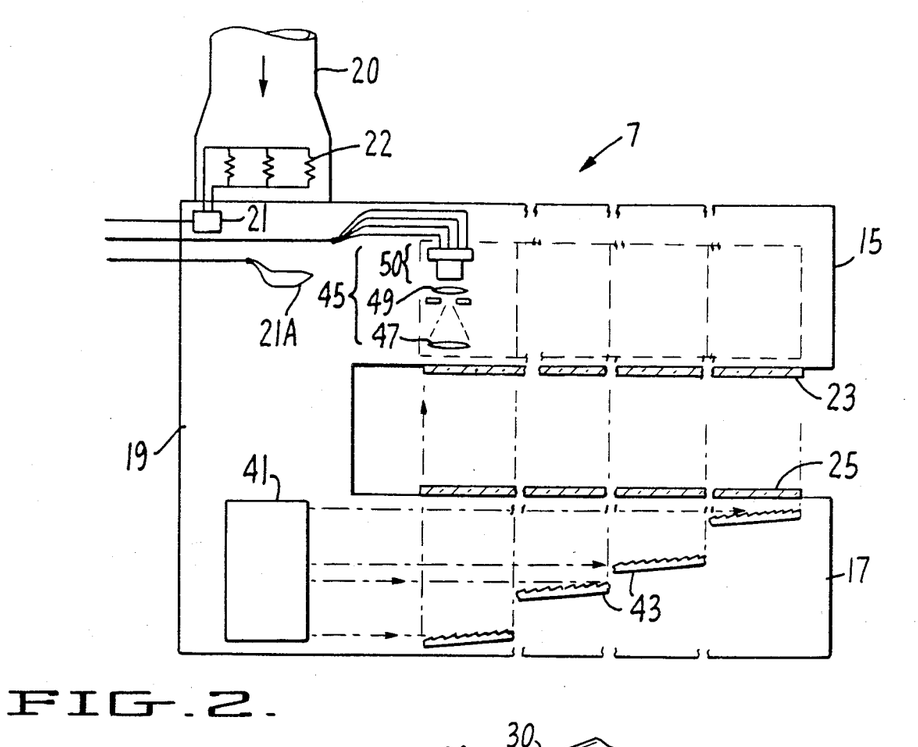
FIG. 2 is a generally schematic diagram of a machine that operates according to the present invention. This diagram is generally oriented as a vertical cross-section taken lengthwise through the machine of FIG. 1.

In practice, it is preferred that heated air be continuously blown into ducts 15 and 17. Thus, in the embodiments of machine 7 in FIGS. 1, 2 and 5, ducts 15 and 17 are connected in gas flow communication with a cross duct 19, and pressurized air is provided to the ducts via inlet duct 20. Thermostatic controls 21 and heaters 22, shown schematically in FIG. 2, are provided in housing 11 to provide the heated air at temperatures sufficiently above dew point temperature (usually about 100° F.) to prevent condensation from forming on the surfaces of ducts 15 and 17. In practice, thermostatic control 21 operates in response to outputs from a conventional thermistor 21A, and heater 22 is a conventional electric heater proportionally controlled by thermistor 21A.

As best shown in FIG. 2, ducts 15 and 17 have transparent walls 23 and 25, respectively, that provide line-of-sight optical communication between the interiors of the ducts. In other words, both the lower horizontal wall 23 of duct 15 and the upper horizontal wall 25 of duct 17 are transparent so that the interior of one of the ducts can be viewed from the interior of the other duct in the absence of web 9. Such line-of-sight communication between the ducts is indicated schematically by the vertical arrows in FIG. 2. In the preferred embodiment, transparent walls 23 and 25 each comprise a single pane of glass, but a series of separate windows formed of glass or other transparent materials can be utilized. In practice, transparent walls 23 and 25 are about three inches wide.

Figures 3, 4:
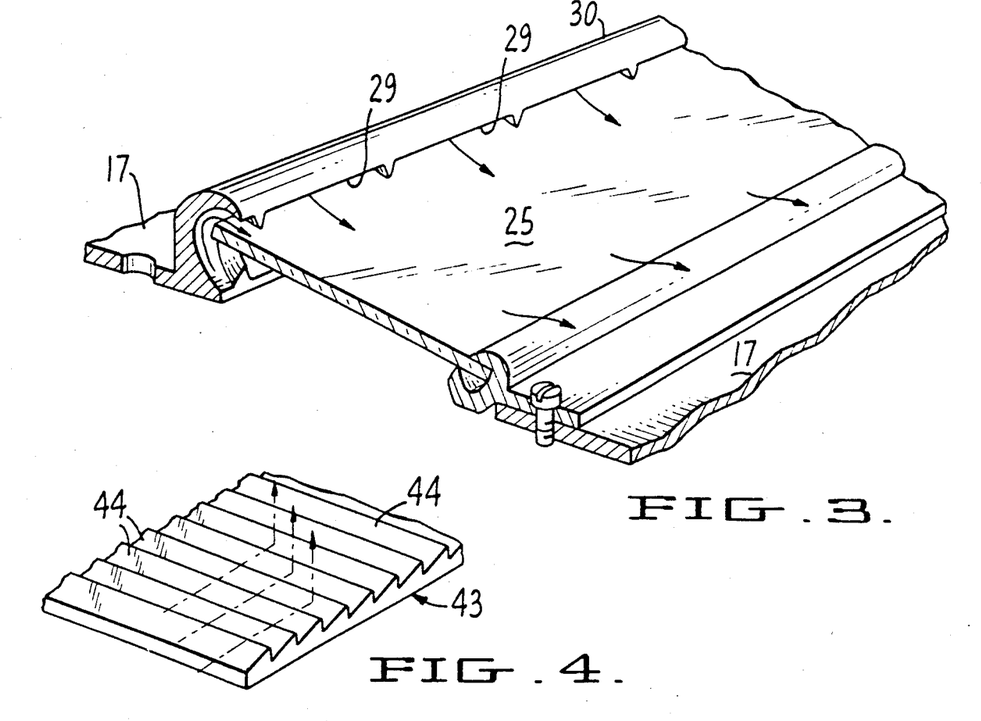
FIG. 3 is a pictorial view, drawn to an expanded scale for purposes of illustration, of certain components of the machine of FIG. 1.
FIG. 4 is a pictorial view of one embodiment of an array of mirrors for use in the machine of FIG. 1.

For practical use of machine 7 in a paper-producing environment, transparent walls 23 and 25 must be kept substantially free from accumulations of dust and other particulates that may interfere with transmission of light through the walls. A suitable particulate-removal device to prevent such accumulations is illustrated in FIG. 3 in conjunction with transparent wall 25. It should be understood that a similar particulate-removal device is provided to keep transparent wall 23 free from accumulations of particles. Generally speaking, the particulate-removal device in FIG. 3 produces air flows, indicated by the curved arrows, that continuously sweep the exterior surfaces of transparent wall 25. More particularly, the particulate removal means includes open-ended channels 29 formed at spaced-apart locations in an elongated frame member 30 that supports one side of wall 25. The exterior open ends of channels 29 are oriented to direct flows of pressurized air across the exterior surface of wall 25 as indicated. The interior open ends of channels 29 are in gas-flow communication with the interior of duct 17 to receive air flow driven by pressurized air carried by the duct. Preferably, channels 29 are spaced along the full length of transparent walls 23 and 25, and transparent walls 23 and 25 are slightly canted from horizontal to promote water drainage from their surfaces.

Further for practical use of machine 7 in a paper-producing environment, convenient access must be provided to its components for repair and maintenance. Thus, in the embodiment of FIG. 1, doors 32 are mounted along the length of ducts 15 to provide access to the interior of the duct. Additionally, in the embodiment in FIG. 5, sliding tray-like mechanisms 33 are mounted to extend lengthwise within upper and lower ducts 15 and 17 to carry the measurement instruments and components. The tray-like mechanisms 33 each have a box-like configuration and include runners, or the like to guide the tray-like mechanisms within ducts 15 and 17. To gain access to the instruments and components, the ends of duct 15 and 17 are opened and tray-like mechanisms 33 are slidably removed as indicated by dashed lines in FIG. 5.

Figure 7:
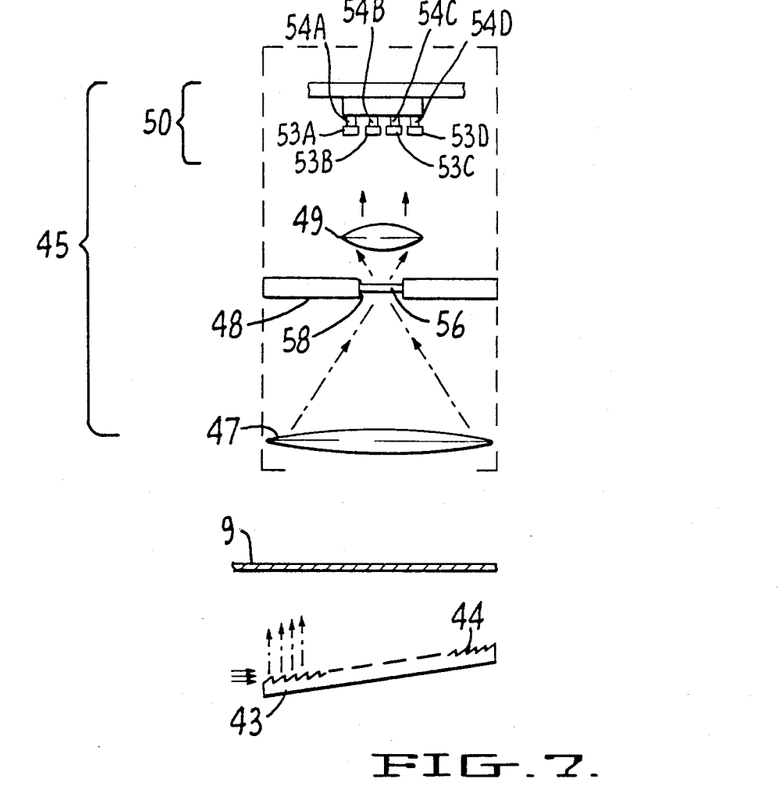
FIG. 7 is a detailed view, drawn to an enlarged scale for purposes of explanation, of a light detection assembly for use in the machine of FIG. 1.

The components of machine 7 for providing optical measurements of a traveling web of sheet material are best illustrated in FIGS. 2, 4 and 7. Referring first to FIG. 2, the optical components include a light source 41 mounted at one end of duct 17, a mirror array 43 mounted along the length of duct 17 to reflect source light through transparent wall 25 along substantially the entire cross-directional extent of web 9, and sets 45 of light detection devices mounted in duct 15 to receive light transmitted through transparent wall 23. In practice, light source 41 is positioned to direct at least two beams of substantially collimated light through duct 17 generally parallel to the longitudinal centerline of the duct, and mirror array 43 is stationarily mounted within duct 17 to receive and decompose the collimated beams to provide parallel rays directed upwardly through transparent wall 25 generally perpendicular to the surface of web 9 along substantially its entire width. In duct 15, the sets 45 of light detection devices are mounted in series, as partially shown in FIG. 7, with the sets 45 spaced apart from each other about every three to six inches across substantially the entire width of web 9.

One embodiment of mirror array 43 is shown in FIG. 4. In this embodiment, mirror array 43 comprises slanting mirror sections 44 mounted on a generally planar base such that, in profile, the mirror sections 44 have a continuous saw-tooth-like configuration. In practice, the angle of each mirror section 44 is about forty-three degrees relative to the base of the array and, in assembled condition, the planar base is mounted in duct 17 at a slight angle from horizontal, usually about two degrees. Thus, in installed condition, mirror arrays 43 extend as a continuous ramp along the length of duct 17 in the path of light beams from source 41 and for the angles mentioned previously, the individual mirror sections 44 then each slant at an angle of about forty-five degrees from horizontal. As a result of this structural relationship, as shown in FIGS. 1 and 2, the collimated beams of light that are generally horizontally incident on the staggered slanting sections 44 along the length of mirror array 43 are decomposed into parallel rays directed substantially vertically. In practice, if web 9 is wider than about eighteen feet, two mirror arrays are utilized and a light source is located at each end of duct 17.

Figures 5, 6:
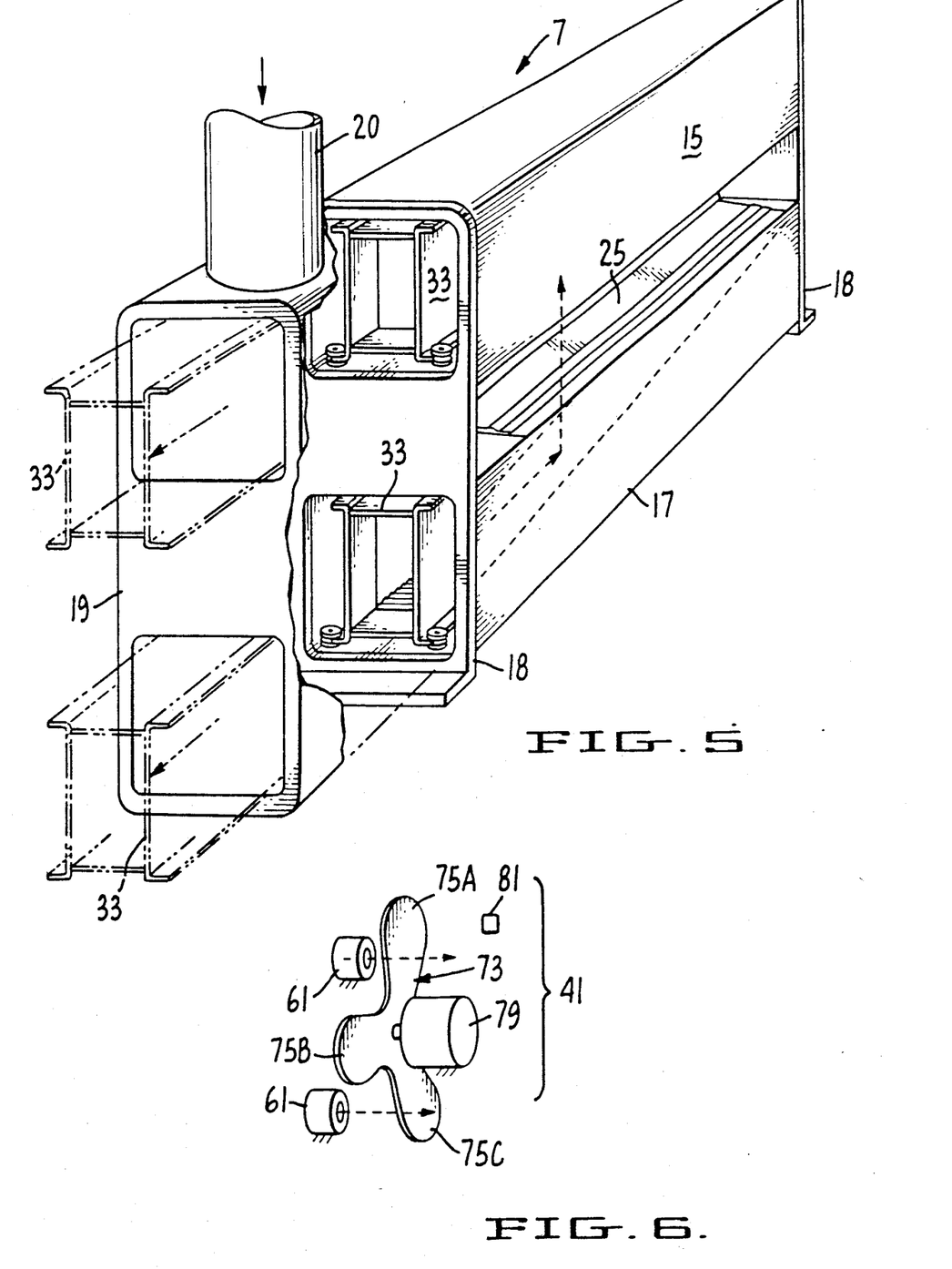
FIG. 5 is a pictorial view, partially cutaway, showing certain internal components of the machine of FIG. 1. In this drawing, components that are in displaced positions are shown by dashed lines.
FIG. 6 is an exploded pictorial view of components comprising a light source assembly for use in the machine of FIG. 1.

In FIG. 6, an assembly comprising a preferred embodiment of light source 41 is shown. In this embodiment, light source 41 includes two illuminating devices 61 fixedly mounted at the end of duct 17. In practice, illuminating devices 61 are conventional incandescent lamps and each includes a parabolic reflector member that forms a collimated beam of generally parallel rays emitted through an appropriate lens mounted at the mouth of the reflector. Preferably, illuminating devices 61 are incandescent lamps that emit a broad band of visible and infrared light including light within the wavelength band between 1.3 and 2.1 microns.

FIG. 6 further shows a mechanism for modulating, or chopping, the beams of light from illuminating devices 61. In the illustrated embodiment, the modulating mechanism includes a rotor member 73 having three symmetrical vanes 75A, 75B, and 75C that radially extend at about 120° intervals from the center of rotation of the rotor member. In machine 7, rotor member 73 is rotatably driven by motor 59 so that vanes 75A, 75B and 75C simultaneously block, or unblock, light from illuminating lamps 61 depending upon the angular position of the vanes.

As also shown in FIG. 6, a stationarily-mounted position detector 81 can be provided to detect the rotational position of vanes 75A, 75B and 75C. Position detector 81 can, for example, be a light-emitting diode combined with a phototransistor (see FIG. 8) mounted to detect passage of light through a small hole in one of the rotor vanes at a predetermined position. Output signals from position detector 81 are used to provide timing and synchronization as will be later explained in detail.

Reference is now be made to FIG. 7 which shows that each set 45 of the light detection devices includes an assembly of components for collimating, filtering and sensing light rays that have been transmitted through web 9 generally perpendicular to the web surface. In the preferred embodiment, the collimating components of the light detection devices include converging lenses 47 and 49, and aperture plates 48. In the detection assemblies, aperture plates 48 are stationarily mounted generally at the focal points of lenses 47; the second converging lenses 49 are mounted beyond the aperture plate 48 by distances approximately equal to the focal length of lenses 49. Lenses 47 and 49 can be, for example, Fresnel-type lenses.

As mentioned above, each set 45 of light detection devices in FIG. 1 includes components for filtering and sensing light. In FIG. 7, sets of those filtering and sensing components are generally indicated by bracket 50. In the illustrated embodiment, each individual set 50 includes four optical bandpass filters 53A-D and four photoelectric transducers 54A-D, respectively. Bandpass filters 53A-D differ from each other in terms of the bands of wavelengths of light that they pass. In fibrous sheet-making operations such as papermaking, for example, the infrared spectrum is usually of primary interest. Specifically, for paper-making processes, bandpass filter 53A is selected to pass light in a narrow band of wavelengths about a mean value of 1.5 microns, bandpass filter 53B is selected to pass light in a narrow band of wavelengths about a mean value of 1.3 microns, bandpass filter 53C is selected to pass light in a narrow band of wavelengths about a mean value of about 1.9 microns, and bandpass filter 53D is selected to pass light in a narrow band of wavelengths about a mean value of 1.8 microns. For convenience, such values as well as alternative values are summarized in the table below.

| Bandpass Filter | Wavelength Passed (mean value) |
| --- | --- |
| 53A | 1.5 or 2.1 microns |
| 53B | 1.3 or 1.8 microns |
| 53C | 1.9 microns |
| 53D | 1.8 microns |

In the discussion that follows, the wavelengths of light passed by bandpass filters 53A and 53C will be called the "measurement" wavelengths and the wavelengths passed by bandpass filters 53B and 53D will be called the "reference" wavelengths. In practice, the measurement wavelengths are selected for preferential absorbtion by the sheet material of web 9 and the reference wavelengths are selected for less substantial absorbtion. In cases where web 9 comprises paper sheet material, for example, one measurement wavelength is normally chosen for specific absorptions by cellulose fibers and one reference wavelength is chosen to be near, but outside, the resonant absorption band of cellulose.

The photoelectric transducers 54A-D in the sets 45 of light detection devices in FIG. 7 are substantially identical. The transducers can, for example, be of the type made from lead sulfide. In assembled condition, transducers 54A are mounted to bandpass filters 53A such that all light reaching the transducers passes through the filters. Likewise, transducers 54B are mounted to bandpass filters 53B such that all light reaching the transducer passes through the bandpass filters. The pairs of transducers and filters 53C-54C and 53D-54D are similarly associated. Thus, in the case where bandpass filters 53A and 53C pass light at the measurement wavelengths, transducers 54A and 54C will receive light only at the measurement wavelength; likewise, in the case where bandpass filters 53B and 53D pass light at the reference wavelengths, transducers 54B and 54D will receive light only at the reference wavelengths. The pairs of bandpass filters and photoelectric transducers are shown to be mounted side by side in the cross direction in FIGS. 2 and 7; however, those pairs could be grouped in other configurations.

In the preferred embodiment of the sets of light detection devices 45, shown in FIG. 7, diffusers 56 are. mounted across apertures 58 in aperture plate 48 to provide mixing of light rays passed through apertures 58. In practice, diffusers 56 are usually thin sheets formed of Teflon. Alternatively, diffusing lenses can be used to mix light rays passing through apertures 58.

Figure 8:
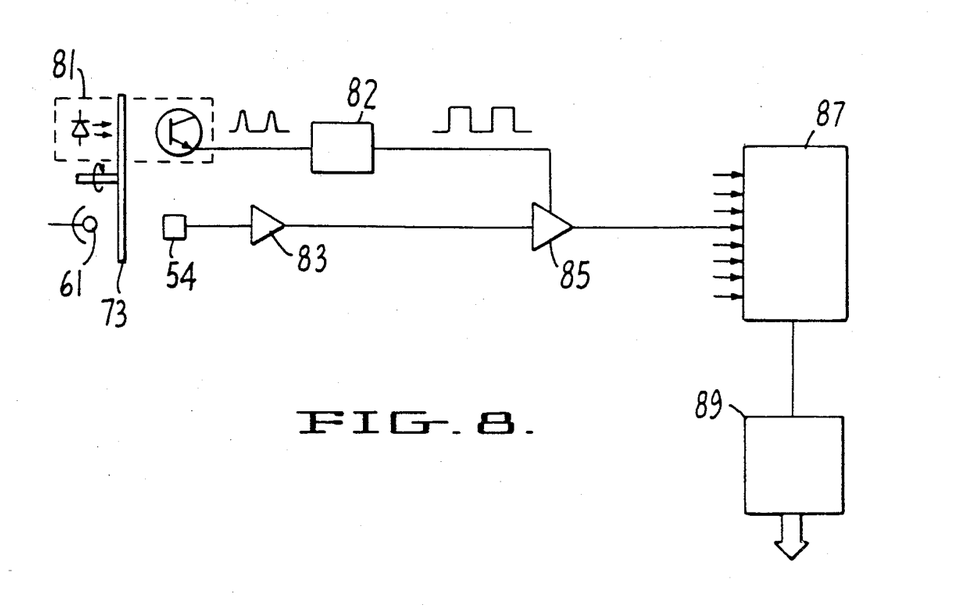
FIG. 8 is a functional diagram of an electronic system for processing signals obtained by the machine of FIG. 1.

Referring now to FIG. 8, a system is schematically shown for processing electrical signals produced by the groups of photoelectric transducers 54A-54D. The purpose of the electronic system is to provide output signals indicative of optical properties of examined profiles of traveling webs. The system in FIG. 8 includes position detector 81 that provides output signals that are indicative of the rotational position of rotor 73. In the illustrated system, the output signals from position detector 81 are conveyed to a pulse converter 82 that converts the signals into square-wave signals to facilitate synchronization of subsequent processing steps.

The system of FIG. 8 further includes a photoelectric transducer 54 connected to a conventional preamplifier 83 that amplifies the electrical output signals from the transducer. Transducer 54 should be understood to be representative of any one of the transducers 54A-D described above. A demodulator 85, using the square-wave position signals from converter 82 for synchronization purposes, is connected to demodulate the output signals for preamplifier 83 and, thereby, to provide direct current signals having amplitudes proportional to the intensity of light received by photoelectric transducer 54. As further shown in FIG. 8, demodulated signals derived from on of the transducers 54 are multiplexed with output signals from other of the transducers 54 (not shown) by a multiplexer 87. The multiplexed signals are converted to digital form by a conventional analog-to-digital converter 89 for further processing. In the system of FIG. 8, the electronic components (i.e., pulse converter 82, preamplifier 83, demodulator 85, multiplexer 87, and analog-to-digital converter 89) are of conventional design and are well known in the signal processing art. In the system, because of narrow bandpass filters 53A-D and because modulation by rotor member 73 is coordinated with pulse converter 82, the analog signals from the sets of transducers 54A-D are substantially undisturbed by extraneous sources of light.

Complete operation of machine 7 of FIG. 1 will now be described with initial emphasis upon the aspects of the machine that render it suitable for use in severe environments such as near the first press section of a paper-making machine. To begin operation of the machine, pressurized air is introduced via inlet duct 20 and is distributed to ducts 15 and 17 via cross duct 19. The atmosphere in ducts 15 and 17 is maintained above ambient temperature by thermostatic control 21 and heater 22. The air blown into duct 15 provides convective cooling of light detection devices 45 and results in heating of the walls of duct 15 to prevent condensation of water vapor on the wall surfaces under normal operating conditions in a papermaking plant. This latter feature has the practical significance of preventing condensation from dropping from the walls of duct 15 onto web 9 or otherwise interfering with operation of machine 7. Further, the air blown into ducts 15 and 17 provides sufficient positive pressure to create air flows that sweep the surfaces of transparent walls 23 and 25, as shown in FIG. 3, to prevent accumulation of particulates on those walls. Still further, the air keeps mirror array 43 free of dust by providing sufficient pressurization to prevent dust particles from entering ducts 15 and 17.

With reference now to FIG. 6, measurement of optical properties of a traveling web 9 of sheet material will be described in the context of providing measurement of parameters such as basis weight, moisture content and dry basis weight. To initiate such measurements, rotor 73 is rotatably driven to modulate the emitted light beams from illuminating devices 61. When light from illuminating devices 61 is not blocked by the vanes of rotor 73, the beams extend along duct 17 and are decomposed and reflected by the staggered slanting section 44 of mirror array 43. The decomposed beams form parallel rays that are directed upward through transparent wall 25 generally perpendicular to the surface of web 9 along the length of mirror array 43. One effect of directing parallel rays perpendicularly to web 9 is that optical measurements of the web's transmissive properties can be substantially independent of its vertical location between ducts 15 and 17. By way of contrast, if the rays incident on web 9 were not perpendicular to the web's surface, the quantity of light detected by photoelectric detectors 54 could vary depending upon the elevation of the web surface. Such variations could be caused, for example, by fluttering of the web and, if present, would complicate accurate determination of the web's optical properties.

Of the rays that pass through web 9, some will emerge generally perpendicular to the web surface (i.e., vertically) and others will be scattered at various angles from vertical. The following discussion will focus on those rays that emerge generally vertical from the surface of web 9 and then pass through transparent wall 23 of upper duct 15. Upon passage through wall 23, the vertical parallel rays are focused by converging lenses 47 toward apertures 56 in plates 48. The apertures select out the parallel rays of light that originate from the area of web 9 directly below lenses 49. After the selected rays pass through apertures 58, they diverge until reaching converging lenses 49 which re-focus the rays generally parallel to each other. The parallel rays then fall upon bandpass filters 53A-D and are detected by the photoelectric transducers 54A-D, respectively, at four distinct narrow bands of wavelengths. Diffusing sheets 56 at apertures 58 assure that rays reaching transducers 54A-D are somewhat diffused and, therefore, substantially representative of the same inspected area of web 9. Further, it can now be understood that because the converging lenses 47, aperture plates 48 and converging lenses 49 generally operate to collect only parallel rays that emerge substantially perpendicular to the surface of web 9, measurements of transmissive properties of web 9 with the above-described system are substantially independent of the web elevation relative to photoelectric transducers 54 and, therefore, are not substantially affected by fluttering of the web.

Typical formulae for calculating dry basis weight (DBW), basis weight (BW) and percent moisture content (MC) of web 9 are as follows, wherein the asterisks indicate multiplication:

$$DBW = A0 + A1*\ln(MES1) - A2*\ln(REF1) + A3*\ln(MES2) - A4*\ln(REF2).$$

$$BW = B0 + B1*\ln(MES1) - B2*\ln(REF1) + B3*\ln(MES2) - B4*\ln(REF2).$$

$$MC = C0 + C1*\ln(MES1) - C2*\ln(REF1) + C3*\ln(MES2) - C4*\ln(REF2).$$

$$\text{Moisture} = 100*MC/BW.$$

In regard to the preceding equations, the signal determined when web 9 is present may be referred to as an "on-sheet" signal, and the signal determined when web 9 is not present may be referred to as an "off-sheet" signal. Thus, MES1 is the on-sheet signal at the first measurement wavelength divided by the off-sheet signal at the same wavelength. Similarly, REF1 is the on-sheet signal level at the first reference wavelength divided by the off-sheet signal level at the same wavelength. Likewise, MES2 is the on-sheet signal level at the second measurement wavelength divided by the offsheet signal at the same wavelength. Finally, REF2 is the on-sheet signal level at the second reference wavelength divided by the off-sheet signal level at the same wavelength.

Further in the above formulae, the coefficients A0, A1, A2, A3 and A4 are constants relating to the dry basis weight. Normally, coefficients A1 and A2 are both positive in sign and are approximately equal in magiitude, and coefficients A3 and A4 are relatively smaller in magnitude than A1 and A2. Likewise, the coefficients B0, B1, B2, B3 and B4 are calibration constants relating to basis weight. Coefficients B1 and B2 are usually both positive in sign and approximately equal in magnitude, and coefficients B3 and B4 are relatively smaller in magnitude than B1 and B2. Similarly, the coefficients C0, C1, C2, C3 and C4 are calibration constants for determination of moisture content. Normally, coefficients C3 and C4 are both positive in sign and approximately equal in magnitude, while C1 and C2 are relatively smaller in magnitude than C3 and C4.

The wavelengths for the MES1 measurements are chosen to be sensitive primarily to the dry basis weight of the paper. In practice, such wavelengths include not only a narrow band of wavelengths about a mean value of 1.5 microns, but also a narrow band of wavelengths about a mean value of 2.1 microns. The REF1 wavelengths are usually chosen at a narrow band of wavelengths about a mean value of 1.3 or 1.8 microns and are used to correct the basis weight measurement for other properties of the paper as well as for effects due to particulates that may fall on the optical surfaces in the system. The MES2 wavelengths are usually chosen at a narrow band of wavelengths about a mean value of 1.9 microns and are sensitive primarily to the water content of paper. The REF2 wavelengths are chosen at a narrow band of wavelengths about a mean value of 1.8 microns and are used to correct the moisture measurements for other properties of paper and for any contaminants on the exposed optical surfaces.

It should be understood that measurements according to the preceding equations are made for each group of transducers 54A-D across web 9. In accordance with the system in FIG. 8, the total of such measurements across a given cross-section of web 9 yields a predetermined sequence of outputs from analog-to-digital converter 89 providing a profile of the web such that the location of each measurement can be readily determined. For example, a measurement made at 4.5 feet from left margin of web 9 can be easily identified. Identification of the location of measurements permits precise control of production conditions at identified cross-directional locations by, for example, automatically controlling slice lip openings at headboxes.

At this point, it should be re-emphasized that the above-described system permits measurements to be taken simultaneously across the full width of web 9. This feature distinguishes the system from scanning type devices that operate to sequentially take measurement across a web. One result of providing non-scanning sensors is that the sequence of readouts of the entire line of detectors can be relatively more rapid than with scanning-type sensors. For example, the non-scanning sensors described above can provide a full profile of sheet 9 in five seconds or less. The capability to quickly perform profile measurements allows rapid actuators to be used and provides much shorter machine control cycles. This is important during startups, grade changes and upsets, but also can reduce machine direction variations in steady-state operation and reduces sensitivity to periodic instabilities.

Although the present invention has been described with particular reference to the preferred embodiment, such disclosure should not be interpreted as limiting. Other alternative embodiments and modifications will no doubt become apparent to those skilled in the art after having read the preceding disclosure. For example, circulation of pressurized air through ducts 15 and 17 can be individually provided and, thus, cross duct 19 might be eliminated. Also, machine 7 may include light collimating devices, such as so-called honeycomb filters, to provide additional collimation of light passing through transparent walls 23 and 25; such filters can further minimize variations due to flutter or other elevation change of web 9 within the vertical gap between ducts 15 and 17. Also, although the preceding description has described a single array of mirrors 43, a multiplicity of mirror arrays can be used. Still further, additional measurements of basis weight and sheet moisture can be made at the reel end of a paper machine and can be used for calibration purposes and to correct for long-term signal drift. As another modification, illuminating devices 61 can be mounted to direct beams of light perpendicular to the side of housing 11 with deflecting mirrors arranged to deflect the beams and direct them generally parallel to the centerline of duct 17 toward mirror arrays 43. As still another modification, modulating devices other than the illustrated rotor 73 can be employed to chop the output light from lamps 61. In fact, the modulating devices can include optical filters such that the modulated light is emitted sequentially at different wavelengths; for example, optical filters at the modulating device could provide light filtered at a narrow band of wavelengths about a mean value of 1.5 microns, followed by light filtered at a narrow band of wavelengths about a mean value of 1.3 microns, then at 1.4 microns and at 1.8 microns. In such a system wherein the modulated light is sequentially filtered at four different wavelengths, the sets 45 of light detection devices could include only a single optical bandpass filter.

In view of the above-described variations and others, it is intended that the appended claims be interpreted as covering all alternative embodiments and equivalents as fall within the spirit and scope of the present invention.

We claim:

1. A system for determining optically-sensitive properties of traveling webs of sheet material during manufacture without scanning, comprising:
   (a) first duct means mounted to extend transversely of one face of a traveling web, the duct means having a transparent wall facing the web;
   (b) light source means arranged to direct collimated light lengthwise along the interior of the first duct means;
   (c) reflector means mounted within the first duct means to reflect said beams as parallel rays directed through said transparent wall generally perpendicular to the surface of the web to illuminate substantially the full width of the web;
   (d) second duct means mounted to extend generally parallel to the first duct means adjacent the opposite face of the web and having a transparent wall facing the sheet; and
   (e) light detector means mounted within the second duct means to detect the intensity of substantially parallel rays emerging from the web surface substantially perpendicular to the surface at least at four different ranges of wavelengths.

2. A system according to claim 1 wherein the reflector means comprising an array of reflecting surfaces having, in profile, a generally saw-tooth configuration.

3. A system according to claim 2 wherein said array is mounted with said surfaces at progressively higher elevations.

4. A system according to claim 3 further including a rotor having spaced-apart vanes to modulate light emitted from said light source means.

5. A system according to claim 1 wherein the detector means comprises sets of at least four photoelectric transducers and associated optical filters with each of said filters being selected to preferentially pass a selected band of wavelengths of light.

6. A system according to claim 5 wherein the detector means further includes collecting means associated with each of said sets to collect the parallel ones of the rays of light transmitted through the web generally perpendicular to its surface directly below said sets.

7. A system according to claim 6 wherein each collecting means includes sets of spaced-apart converging lenses and aperture plates mounted therebetween at distances generally equal to the focal lengths of said converging lenses.

8. A method for optically determining properties such as basis weight, moisture content and dry basis weight of traveling webs of sheet material without scanning comprising the steps of:
- (a) directing rays from at least one beam of light such that rays from the beam are generally parallel and perpendicularly incident upon the surface of a traveling web to simultaneously illuminate substantially the full width of the web;
- (b) detecting the intensity of the parallel rays emerging generally perpendicularly from the web at least at four selected bands of wavelengths; and
- (c) providing electrical output signals proportional to the detected light intensity at each of said different wavelengths.

9. A method according to claim 8 wherein the step of detecting the intensity of rays transmitted through the web is accomplished by a plurality of adjacent detectors such that the intensity of light at least at four selected bands of wavelengths is detected concurrently.

10. A method according to claim 9 further including the step of collecting parallel rays of light transmitted through the web at selected inspection areas and then diffusing the collected rays such that the diffused rays, for all four bands of wavelengths, represent the same inspected area of the web.

11. A method according to claim 8 including the step of computing parameters including dry basis weight, basis weight and moisture content of a traveling web by computing values for the following equations:

$$DBW = A0 + A1*\ln(MES1) - A2*\ln(REF1) + A3*\ln(MES2) - A4*\ln(REF2);$$

$$BW = B0 + B1*\ln(MES1) - B2*\ln(REF1) + B3*\ln(MES2) - B4*\ln(REF2); \text{ and}$$

$$MC = C0 + C1*\ln(MES1) - C2*\ln(REF1) + C3*\ln(MES2) - C4*\ln(REF2).$$

wherein:

DBW is dry basis weight of an inspected are of the web of sheet material;

BW is the basis weight of an inspected area of sheet material;

MC is the moisture content of an inspected area of sheet material;

"ln" is the natural logarithmic function;

MES1 is the detected intensity at a first wavelength band;

REF1 is detected intensity at a second wavelength band;

MEAS2 is detected intensity at a third wavelength band;

REF2 is detected intensity at a fourth wavelength band; and

A0 through A4, B0 through B4, and C0 through C4 are constants.

12. A method according to claim 11 wherein MES1 is the signal level at the first wavelength band when a web is present divided by the signal level when no web is present, REF1 is the signal level at the second wavelength band when a web is present divided by the signal level when no web is present, MEAS2 is the signal level at the third wavelength band when a web is present divided by the signal level when no web is present, and REF2 is the signal level at the fourth wavelength band when a web is present divided by the signal level when no web is present.

13. A method according to claim 12 wherein the wavelength band for MES1 is a narrow band of wavelengths around a mean value of 1.5 microns; the wavelength band for REF1 is a narrow band of wavelengths around a mean value of 1.3 microns; the wavelength band for MES2 is a narrow band of wavelengths around a mean value of 1.9 microns; and the wavelength band for REF2 is a narrow band of wavelengths around a mean value of 1.8 microns.

14. A method according to claim 12 wherein the wavelength band for MES1 is a narrow band of wavelengths around a mean value of 2.1 microns; the wavelength band for REF1 is a narrow band of wavelengths around a mean value of 1.8 microns; the wavelength band for MES2 is a narrow band of wavelengths around a mean value of 1.9 microns; and the wavelength band for REF2 is a narrow band of wavelengths around a mean value of 1.8 microns.

* * * * *